United States Patent [19]

Kobayashi et al.

[11] Patent Number: 4,966,030
[45] Date of Patent: Oct. 30, 1990

[54] PIN-ON-DISK TYPE WEAR TESTING DEVICE

[75] Inventors: Takashi Kobayashi; Eiji Suzuki, both of Osaka; Yoshitaka Uchiyama, Toyama, all of Japan

[73] Assignee: Starlite Co., Ltd., Osaka, Japan

[21] Appl. No.: 417,642

[22] Filed: Oct. 5, 1989

[30] Foreign Application Priority Data

Oct. 11, 1988 [JP] Japan .................. 63-256335

[51] Int. Cl.$^5$ ............................. G01N 3/56
[52] U.S. Cl. ........................................ 73/7
[58] Field of Search ........................ 73/7–10

[56] References Cited

FOREIGN PATENT DOCUMENTS 497306 12/1938 United Kingdom .............. 73/10

*Primary Examiner*—Robert Raevis
*Attorney, Agent, or Firm*—Ratner & Prestia

[57] ABSTRACT

A pin-on-disk type wear testing device which has a non-contact type displacement gauge that moves integrally with the pin type testpiece sliding against the disk type testpiece, so that the said pin-on-disk type wear testing device of the present invention can accurately measure the displacement of the pin type testpiece with respect to the disk type testpiece without being affected by the waving motion of the disk type testpiece, the thermal expansion of the whole device, and other factors, thus making it possible to accurately measure the amount of wear of the pin type testpiece.

3 Claims, 2 Drawing Sheets

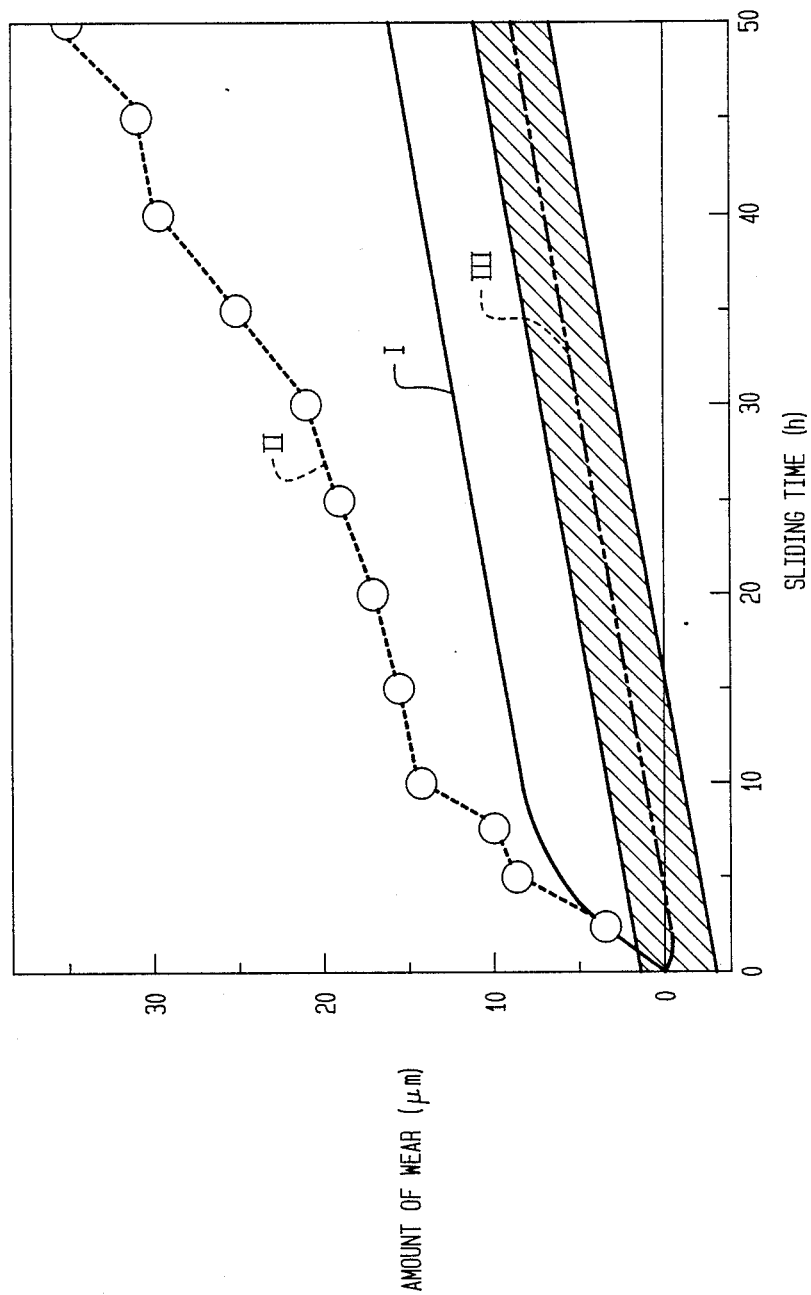

PIN-ON-DISK TYPE WEAR TESTING DEVICE

BACKGROUND OF THE INVENTION

1. Field of the invention:

The present invention relates to a wear testing device used for measuring the amount of wear of a sliding material, and more particularly, to a pin-on-disk type wear testing device in which a pin type testpiece is in contact with a rotating disk under a constant load for measuring the amount of wear of the pin type testpiece.

2. Description of the prior art:

As a wear testing device for measuring the amount of wear of a sliding material, a pin-on-disk type wear testing device is known in which a pin type testpiece to be measured for wear is stationarily in contact with a rotating disk type testpiece for measuring the rate of wear of the pin type testpiece with respect to time. With the pin-on-disk type wear testing device, the following two kinds of methods for measuring the wear rate have been used: Method "A" in which the rate of weight loss from the pin type testpiece which slides against the rotating disk type testpiece is measured with respect to time to calculate the rate of wear with respect to time; and Method "B", as shown in FIG. 3, a rotating disk type testpiece 13 is mounted on a disk type testpiece table 12 that is supported in a base 11 to which a contact or noncontact type displacement gauge 18 is fixed for detecting the progressive amount of displacement between the base 11 and a pin type testpiece 14 in contact with the disk type testpiece 13 under a constant load, and the amount of wear of the pin type testpiece 14 is measured by the amount of displacement.

In method "A", since the pin type testpiece must be dismounted from the wear testing device at specified intervals of time for measurement of its weight and then refitted to the wear testing device for continued testing, the test efficiency is greatly sacrificed. Moreover, when the pin type testpiece once dismounted is refitted to the wear testing device, the pin type testpiece cannot be positioned to contact the disk type testpiece at the same position where it had been in contact with the disk type testpiece before the removal therefrom, with a resultant change in the condition of the wear debris existing between the pin type testpiece and the disk type testpiece, hampering accurate measurement of the wear of the pin type testpiece with respect to time. Furthermore, at the time of the weight measurement, if the pin type testpiece absorbs moisture with a resultant change in its weight, it is not possible to accurately measure the amount of wear of the pin type testpiece.

On the other hand, method "B" allows continuous measurement of the wear rate of the pin type testpiece with respect to time. However, since the displacement gauge 18 is fixed to the base 11 of the wear testing device, the amount of displacement measured by the displacement gauge 18 represents the absolute displacement with respect to the base 11. This means that the amount of displacement measured by the displacement gauge 18 includes not only the wear loss $\Delta h$ of the pin type testpiece but also the error $\Delta h'$ caused by the displacement of the disk type testpiece with respect to the base 11. The cause of the error $\Delta h'$ includes the displacement caused by an axial positional change of the disk type testpiece 13 due to its rotational motion, a circumferential waving motion of the disk type testpiece 13, and the thermal expansion of whole device due to thermal changes such as heat generation through the friction between the pin type testpiece and the disk type testpiece, all of which combine to prevent accurate measurement of the wear rate of the pin type testpiece 14 with respect to time.

SUMMARY OF THE INVENTION

The pin-on-disk type wear testing device of this invention, which overcomes the above-discussed and numerous other disadvantages and deficiencies of the prior art, is a pin-on-disk type wear testing device in which a pin type testpiece is stationarily in contact with a rotating disk type testpiece under a constant load, the pin type testpiece sliding against the disk type testpiece along a given circular track thereon, to measure the wear rate of the pin type testpiece with respect to time, the pin-on-disk type wear testing device comprising: a pin type testpiece holder for holding the pin type testpiece in such a way as to move integrally therewith; and a non-contact type displacement gauge fixed to the pin type testpiece holder in such a way as to face the disk type testpiece, for detecting the relative displacement of the pin type testpiece holder with respect to the disk type testpiece.

In a preferred embodiment of the invention, the non-contact type displacement gauge is so mounted as to face a position adjacent to a position where the pin type testpiece is sliding against the disk type testpiece along the circular track thereon, for detecting the relative displacement of the facing position on the disk type testpiece with respect to the pin type testpiece holder.

In a preferred embodiment of the invention, the disk type testpiece is rotated integrally with a disk type testpiece table which is rotatably supported in a base.

Thus, the invention described herein makes possible the objective of providing a pin-on-disk type wear testing device which has a non-contact type displacement gauge that moves integrally with the pin type testpiece sliding against the disk type testpiece, so that the said pin-on-disk type wear testing device of the present invention can accurately measure the displacement of the pin type testpiece with respect to the disk type testpiece without being affected by the waving motion of the disk type testpiece, the thermal expansion of the whole device, and other factors, thus making it possible to accurately measure the amount of wear of the pin type testpiece.

BRIEF DESCRIPTION OF THE DRAWINGS

This invention may be better understood and its numerous objects and advantages will become apparent to those skilled in the art by reference to the accompanying drawings as follows:

FIG. 4 is a graph showing the results of measurement by the pin-on-disk type wear testing device of the present invention as compared with the conventional pin-on-disk type wear testing device.

DESCRIPTION OF THE PREFERRED EMBODIMENTS

Figure 2:
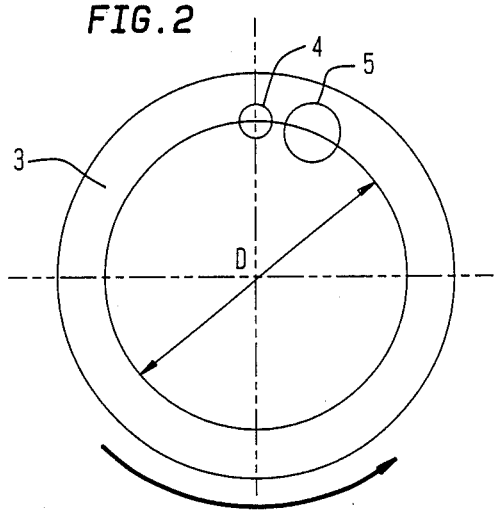
FIG. 2 is a plan view showing the positional relationship between each of a pin type testpiece and a displacement gauge and a disk type testpiece in the above pin-on-disk type wear testing device.
Figure 1:
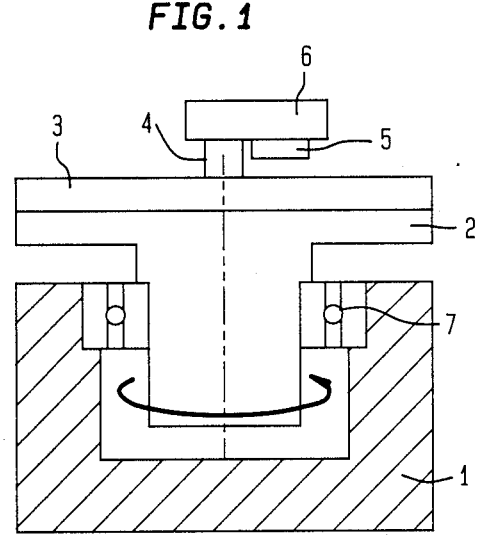
FIG. 1 is a cross sectional view showing a pin-on-disk type wear testing device of the present invention.

FIG. 1 shows a pin-on-disk type wear testing device of the present invention, which includes a testpiece table 2 rotatably supported in a base 1 by means of a ball bearing 7. The testpiece table 2 has an approximately planar top surface on which a disk type testpiece 3 is mounted for integral rotation therewith. As shown in FIG. 2, a pin type testpiece 4 is stationarily in contact with the rotating disk under a constant load at a position away from the rotational center thereof by a given length, the pin type testpiece 4 sliding against the disk type testpiece 3 along a circular track of a given diameter D by the rotation of the disk type testpiece 3. The pin type testpiece 4 is fixed to a pin type testpiece holder 6 which is disposed stationarily with respect to the rotating disk type testpiece 3, the pin type testpiece holder 6 moving integrally with the pin type testpiece 4 in the vertical direction to follow the vertical movement of the pin type testpiece 4.

Mounted to the pin type testpiece holder 6 is a non-contact type displacement gauge 5. The non-contact type displacement gauge 5 is so mounted as to face a position adjacent to a position where the pin type testpiece 4 slides against the disk type testpiece 3 along the circular track thereon, for measuring the relative displacement of the facing position on the disk type testpiece 3 with respect to the pin type testpiece holder 6. The amount of wear of the pin type testpiece 4 is measured with respect to time on the basis of the measurement by the non-contact type displacement gauge 5.

In the pin-on-disk type wear testing device of the present invention with the above-mentioned construction, the pin type testpiece 4 is stationarily in contact with the rotating disk type testpiece 3 under a constant load for sliding along the specified circular track thereon, thus generating progressive wear of the pin type testpiece 4. The non-contact type displacement gauge 5 is mounted to the pin type testpiece holder 6, to which the pin type testpiece 4 is fixed, to continuously measure the displacement of the pin type testpiece holder 6 with respect to the position adjacent to the position where the pin type testpiece 4 is sliding against the disk type testpiece 3 along the circular track thereon, and the displacement measured by the displacement gauge 5 with respect to time is measured as the rate of wear of the pin type testpiece 4 with respect to time.

Since the non-contact type displacement gauge 5 is fixed to the pin type testpiece holder 6 which moves integrally with the pin type testpiece 4 to follow the vertical movement thereof, if the disk type testpiece 3 exhibits a waving motion in its circumferential direction, the displacement gauge 5 is prevented from being affected by the waving motion of the disk type testpiece 3, the pin type testpiece 4 moving to follow the waving motion thereof and therefore the pin type testpiece holder 6 moving to follow the movement of the pin type testpiece 4. Also, if the whole device is deformed due to thermal expansion, the displacement of the disk type testpiece 3 due to the deformation is prevented from being measured by the displacement gauge 5. Thus, the pin-on-disk type wear testing device of the present invention is capable of accurately measuring the wear rate of the pin type testpiece 4.

(EXAMPLE)

For use as a pin type testpiece, 90% by weight of polyacetal and 10% by weight of polytetrafluoroethylen (PTFE) were mixed and molded by injection to produce a pin shaped material 3 mm in length and 5 mm in diameter. A stainless steel material (SUS 303, surface roughness Ra =0.1 μm ±0.05 μm) was formed in a shape 10 mm in thickness and 100 mm in diameter, to use as a disk type testpiece. The diameter of the circular track along which the pin type testpiece was to slide against the disk type testpiece was determined at 85 mm, the contact pressure between the pin type testpiece and the disk type testpiece at 0.3 MPa, the sliding speed of the pin type testpiece (the rotating speed of the disk type testpiece) at 0.5 m/s, and the test temperature at 23° C., and the amount of wear of the pin type testpiece was measured by the above described pin-on-disk type wear testing device of the present invention. The results are shown in the graph of FIG. 4 as wear progress curve I.

Figure 3:
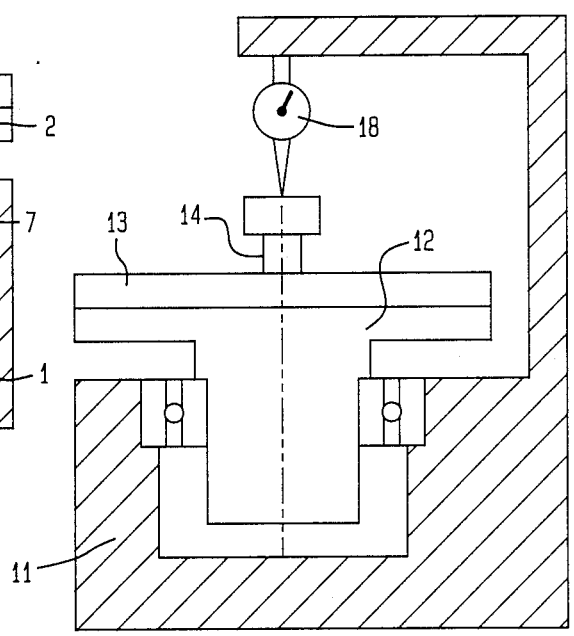
FIG. 3 is a cross sectional view showing a conventional pin-on-disk type wear testing device.

For comparison, the amount of wear of the pin type testpiece was measured by the previously described method "A" in which the loss of weight from the pin type testpiece sliding against the rotating disk type testpiece is measured, as well as by the device shown in FIG. 3 (method "B"). The results are shown in the graph of FIG. 4 as wear progress curves II and III, respectively.

The wear progress curve I for the pin type testpiece measured by the wear testing device of the present invention shows a stable progress with respect to time, indicating accurate measurement of the amount of wear of the pin type testpiece. On the other hand, in method "A", since the weight of the pin type testpiece is measured when the pin type testpiece dismounted from the wear testing device, and then the pin type testpiece is refitted to the wear testing device, the position at which the pin type testpiece slides against the disk type testpiece changes, the effect being shown in the measurement. Method "B" is susceptible to the error caused by such factors as axial motion of the disk type testpiece and thermal expansion of the whole device, and in some cases, causes a phenomenon in which a negative value is given as the wear value in the early stage of the wear. Furthermore, the circumferential waving motion of the disk type testpiece affects the measurement, causing the wear progress curve to greatly fluctuate so as to hamper accurate measurement.

As described above, the pin-on-disk type wear testing device of the present invention is capable of providing highly reliable measurement.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. A pin-on-disk type wear testing device in which a pin type testpiece is in contact with a rotating disk type testpiece under a constant load, the pin type testpiece sliding against the disk type testpiece along a given circular track thereon, said pin-on-disk type wear testing device comprising: a pin type testpiece holder for holding the pin type testpiece in such a way as to move integrally therewith; and a non-contact type displacement gauge fixed to the pin type testpiece holder in such a way as to face the disk type testpiece, for detecting the relative displacement of the pin type testpiece holder with respect to the disk type testpiece, whereby the wear rate of the pin type testpiece with respect to time is measured.

2. A device according to claim 1, wherein said non-contact type displacement gauge is so mounted as to face a position adjacent to a position where the pin type testpiece is sliding against the disk type test-piece along the circular track thereon, for detecting the relative displacement of the facing position on the disk type testpiece with respect to the pin type testpiece holder.

3. A device according to claim 1, wherein said disk type testpiece is rotated integrally integrally with a disk type testpiece table which is rotatably supported in a base.

* * * * *